March 16, 1976 R. S. MOORE Plant Pat. 3,844
MINIATURE ROSE PLANT
Filed Oct. 7, 1974
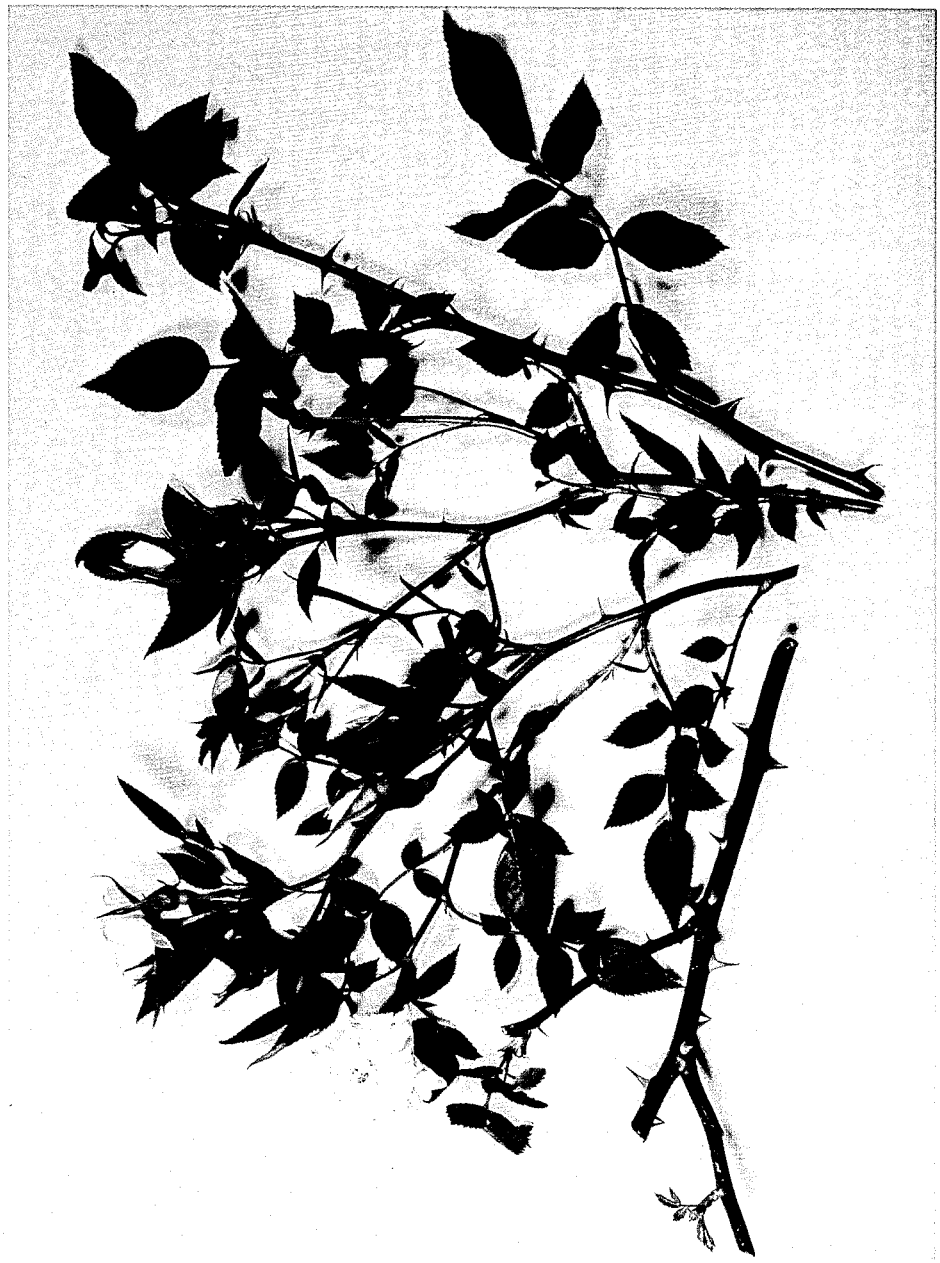

United States Patent

Plant Pat. 3,844

Patented Mar. 16, 1976

3,844

MINIATURE ROSE PLANT

Ralph S. Moore, 2519 E. Noble Ave., Visalia, Calif. 93277

Filed Oct. 7, 1974, Ser. No. 512,629

Int. Cl. A01h 5/00

U.S. Cl. Plt.—8 1 Claim

The present invention relates to a new and distinct variety of hardy, dwarf, bush type rose plant of the miniature class; the variety being primarily characterized—as to novelty—by double white flowers which, as compared to "White Angel" (Plant Pat. No. 3,538), are similar in form but the bud color tends to be pinkish rather than yellowish and fully open flowers tend to have a higher more rounded center.

The variety is further characterized by:

An abundance of bloom, with flowers on mature plants usually borne in loose spray or cluster.

A plant which is vigorous, of rounded compact habit, with semi-glossy, medium green leaves;

A plant which has a normal average height of about 12" to 16" at maturity, resembling the general plant habit of White Angel (Plant Pat. No. 3,538) miniature rose.

A plant which grows and blooms satisfactorily in the greenhouse, outdoors, in pots or in the garden; and provides attractive cut flowers.

The present variety of miniature rose was originated by me at my nursery located at Visalia, Calif., under conditions of careful control and observation, as a cross of un-named seedlings: (*Rosa wichuraiana* × Floradora) × (Little Darling (Floribunda, Pat. 1,581, expired) × red seedling miniature)—all unpatented except as noted.

Subsequent to origination of the variety I successfully asexually reproduced it in my nursery located as aforesaid, by budding as well as by cuttings; the reproductions having run true in all respects.

The color photograph illustrates the variety, including foliage, buds and flowers. Referring now specifically to the new and distinct variety of miniature rose plant, the following is a detailed description thereof in outline; all major color identifications being by reference to the British Colour Council Horticultural Colour Chart, except where common terms of color definition are employed.

Type: Hardy; dwarf; bush; seedling; outdoors; greenhouse, garden decoration; cut flowers.

Class: Miniature.

Flowers:

*Continuity.*—Continuous repeat bloom during normal growing season. May be flowered out of season in greenhouse.

*Fragrance*—Some; sweet.

Flowers borne: Singly and in small cluster on young plants; and usually in clusters, on medium length slender stem on mature plants.

Quantity of bloom: Abundant; repeat bloom throughout normal growing season.

Bud:

*Peduncle.*—Medium length; sturdy; erect; medium to light green. Before calyx breaks—size—small. Form; long pointed, usually with a few short appendages on surface of the bud; with foliaceous parts extending beyond the tip of the bud equal to one-half or more of its length. Color: medium green. As calyx breaks: color—white tinted pale pink. As first petal opens: size—small. Form: medium pointed. Color—outside: near greenish-white at base shading into near rose pink 427/3 at tip. Inside: same as outside. Opening: usually opens well in all weather.

Bloom:

*Size when fully open.*—Small about 3.3 cm. (1¼").

*Petalage.*—double, varies with the season but averages about 40 petals, plus several small petaloids. Form—full—with stamens usually mixed with petaloids. Petals arranged in loose informal pattern.

Petals: Satiny on upper surface; satiny on lower surface.

*Shape.*—Outside petals broad lanceolate with rounded tip; intermediate—lanceolate with rounded tip; inside—lanceolate but not always of regular shape.

Color: Newly opened flower from plant grown in plastic greenhouse (September 1974), Visalia, Calif.

Outside petal: Outside surface—white shading into near white at base. Inside surface—white.

Intermediate petal: Outside surface—same as outside petal. Inside surface—same as outside petal.

Inner petal: Outside surface—same as intermediate petal. Inside surface—same as intermediate petal. General color effect—Newly opened flower—white. Three days open—still white. Behaviour—petals persist for short time then drop off clean. Flower longevity (August 1974) bush in garden 4 to 5 days or longer. Cut flowers kept at living room temperature—3 days.

Reproductive organs:

*Stamens.*—Normal.

*Anthers.*—Normal.

*Pollens.*—Some.

*Pistils.*—Moderate number.

*Styles.*—Fairly even, medium to short length, bunched.

*Stigma.*—Usually well formed.

*Ovaries.*—All enclosed in calyx.

*Hips.*—Few or none.

Foliage:

*Leaves.*—Compound of 5 (sometimes 3) leaflets; abundant, small, leathery, semi-glossy.

*Leaflets.*—Shape; broad lanceolate, apex acute, base less acute. Margin serrate. Color: medium to light green; new leaves sometimes lightly margined bronze. Rachis: slender; upper surface grooved with several very short hairs or prickles; under side sparsely thorny. Stipules: medium length; medium width; medium length, very slender points, turning out at an angle of about 45 degrees.

Growth:

Habit.—Compact; bushy; moderately spreading; much branched.

*Growth.*—Vigorous.

*Canes.*—Medium; slender.

*Main stems.*—Color: medium green.

*Thorns.*—Sparse to moderately thorny; medium size oval base; medium length; slender; hooked slightly downward. Color—brown.

*Prickles.*—None. Hairs: none.

*Branches.*—Color: medium green. Thorns: sparsely thorny; medium length; slenders; hooked slightly downward; medium oval base; color—brown.

*New shoots.*—Color: medium to bright green, sometimes lightly tinted reddish; Thorns: sparsely thorny; medium to long, slender; hooked slightly downward; oval base. Color: light green to brown. Prickles: none. Hairs: none.

The miniature rose plant and its flowers as herein described may vary slightly in detail due to climatic, soil and cultural conditions under which the variety may be grown; the present description being of the variety as grown at Visalia, Calif.

The following is claimed:

1. A new and distinct variety of miniature rose plant of hardy, dwarf, rounded, much branched, bush type, substantially as illustrated and described, characterized by pointed white buds with long green sepals and double white flowers resembling the White Angel (Plant Pat. No. 3,538) miniature rose in general form of bud and flower; the petals being more rounded at the tips and the buds often flushed with soft pink; and further characterized by a plant, easy to propagate from cuttings, of vigorous growth, compact habit, healthy, disease resistant foliage, with buds and flowers produced in above average abundance in loose spray or cluster.

No references cited.

ROBERT E. BAGWILL, Primary Examiner